United States Patent [19]

Gordon

[11] Patent Number: 5,403,578
[45] Date of Patent: Apr. 4, 1995

[54] STABLE TOOTH AND GUM DENTIFRICE WITH MICROENCAPSULATION AND METHOD FOR MAKING SAME

[76] Inventor: Norman Gordon, 114 Sussex Rd., New Rochelle, N.Y. 10804

[21] Appl. No.: 193,440

[22] Filed: Feb. 8, 1994

[51] Int. Cl.⁶ .......................... A61K 7/16; A61K 7/20; A61K 33/40; A61K 33/08
[52] U.S. Cl. ........................................ 424/53; 424/613
[58] Field of Search .................................. 424/53, 613

[56] References Cited

U.S. PATENT DOCUMENTS

| | | | |
|---|---|---|---|
| 4,067,787 | 1/1978 | Kastening et al. | 204/84 |
| 4,094,758 | 6/1978 | Fletcher et al. | 423/582 |
| 4,101,644 | 7/1978 | Frosch et al. | 423/581 |
| 4,237,147 | 12/1980 | Merten et al. | 423/430 |
| 4,311,528 | 1/1982 | Dietz et al. | 106/35 |
| 4,399,633 | 8/1983 | Haughey et al. | 423/583 |
| 4,522,805 | 6/1985 | Gordon . | |
| 4,837,008 | 6/1989 | Rudy et al. . | |
| 4,897,258 | 1/1990 | Rudy et al. . | |
| 4,971,782 | 11/1990 | Rudy et al. . | |
| 4,980,154 | 12/1990 | Gordon . | |
| 5,000,942 | 3/1991 | Libin | 424/53 |

*Primary Examiner*—Shep K. Rose
*Attorney, Agent, or Firm*—Arthur T. Fattibene; Paul A. Fattibene

[57] ABSTRACT

An improved tooth and gum paste formed as a stable, single component composition that includes a non-aqueous carrier containing urea, hydrated silica, fluoride, sodium bicarbonate, pyrophosphate, and a peroxide, one or more of the ingredients being microencapsulated and which in use functions as an aid in preventing periodontal disease by reducing incidents of plaque as well as controlling tartar formation, and also as an aid in preventing dental caries and oral odors; and the method of compounding such improved tooth and gum paste.

6 Claims, 1 Drawing Sheet

STABLE TOOTH AND GUM DENTIFRICE WITH MICROENCAPSULATION AND METHOD FOR MAKING SAME

FIELD OF INVENTION

This invention relates to an improved tooth and gum dentifrice and method of formulating the same, and more specifically to a dentifrice in the form of a stable paste that includes a microencapsulated peroxide in combination with a sodium bicarbonate and a fluoride for minimizing incipient periodontal disease by aiding in the reduction of plaque and tartar, as well as preventing the formation of dental caries, reducing oral odors and brightening the tooth enamel.

PRIOR ART

It has been well known in the dental profession that hydrogen peroxide, baking soda and common table salt have been frequently recommended by dentists for oral hygiene. A leading proponent of such treatment for maintaining oral hygiene has been Dr. Paul Keyes. The disadvantage of this suggested treatment was that the patient or user had to mix these ingredients each time to prepare a fresh preparation at the time of use. Another disadvantage was that the hydrogen peroxide, when combined with baking soda, reacted to rapidly decompose. The mixture was relatively tedious to prepare and cumbersome to use. As a result, the user or patient would quickly tire of preparing such mixture for the time necessary to achieve any beneficial results.

Efforts have been made to achieve the beneficial effects of such treatment by attempts to formulate a single component toothpaste that incorporated a peroxide and a bicarbonate, with or without common table salt, so as to overcome the disadvantage of the so called "Keyes Technique." Such known efforts are disclosed in U.S. Pat. Nos. 4,837,008; 4,897,258 and 4,971,782; where the instability of combining a peroxide and a bicarbonate in a single paste composition has been noted; and the disclosures of some efforts to overcome the instability of such combination. However, the various examples disclosed therein are not known to have been commercially utilized, as the desired commercial stability does not appear to have been achieved thereby.

This invention relates to improvements in tooth and gum dentifrice previously disclosed in my prior U.S. Pat. No. 4,522,805 granted Jun. 11, 1985 entitled Tooth and Gum Dentifrice, and more particularly to improvements to the dentifrice disclosed in my prior U.S. Pat. No. 4,980,154 granted Dec. 25, 1990 entitled Tooth and Gum Dentifrice Composition and Method of Making Same.

While the tooth and gum dentifrice disclosed in my above prior noted patents proved effective for their intended purpose, experience has shown that these formulations can be further improved; particularly with respect to fortifying the dentifrice with a sodium fluoride and hydrated silica to further enhance the stability of the composition. It has been well known that the use of baking soda, hydrogen-peroxide and fluorides enhances oral hygiene. These ingredients independently have been almost universally recommended by dentists for oral hygiene. However, because of the reaction and/or instability of a peroxide with baking soda, maintaining the stability of a single component composition containing these ingredients is a paramount consideration. Accordingly, this invention is directed to further improvements in tooth and gum paste of the type disclosed in my prior U.S. Pat. No. 4,980,154, to further achieve the desired degree of commercial stability.

OBJECTS

An object of this invention is to fortify the tooth and gum paste with a fluoride and hydrated silica in a composition containing microencapsulated peroxide and/or sodium bicarbonate to provide for enhanced stability.

Another object of this invention is to provide a method whereby the various ingredients of the improved tooth and gum paste including the peroxide and bicarbonate are combined in a manner to ensure the stability of the final compounded paste that also includes an active fluoride ingredient.

SUMMARY OF THE INVENTION

The foregoing objects and other features and advantages are achieved by a tooth and gum dentifrice formulated as a stable paste comprising approximately 10 to 30% by weight of hydrated silica (Zeodent), 15 to 35% by weight of sodium bicarbonate, which may be microencapsulated, approximately 3 to 11% by weight of microencapsulated calcium peroxide, approximately 0.125 to 3% by weight of a fluoride in either its natural or microencapsulated form, approximately 0.5 to 3% by weight of urea, which may also be microencapsulated, and the remainder or approximately 40% to 78% by weight of a vehicle or carrier that includes a glycerine, humectant (sorbitol), a thickening agent or binder, whitener, preservative, surfactant, an anti-tartar controller, e.g. pyrophosphate and a flavoring agent. The thickening agent and flavoring agent may be either natural or synthetic or a combination thereof.

IN THE DRAWINGS

DETAIL DESCRIPTION

This invention is directed to an improved form of a tooth and gum dentifrice composed of selected ingredients having known oral hygienic efficiency in their own individual capacity which are combined in the form a stable single component paste composition to synergistically result in a chemical and mechanical action to effect the removal and/or minimizes the build up of plaque and/or tartar on the teeth and to reduce the level of bacteria in the mouth. The resultant effect is to aid in the control and removal of incipient periodontal disease as well as to aid in the reduction of dental caries, mouth odors, and to remove surface stains and tartar on the tooth surface to leave it cleaner and brighter.

Essentially, the improved tooth and gum dentifrice of this invention comprises a single paste composition containing sodium bicarbonate which may be microencapsulated, microencapsulated calcium peroxide, urea, hydrated silica (Zeodent), a fluoride, e.g. a sodium fluoride, sodium monofluorophosphate or stannous fluoride, in a paste carrier or vehicle which includes a humectant (sorbitol), surfactant, a tartar inhibitor, a preservative, a thickening agent or binder and a suitable flavoring agent. The preferred calcium peroxide is one in a water free base. Microencapsulation as used herein refers to particle sizes in the range of 10 to 200 microns.

Figure 1:
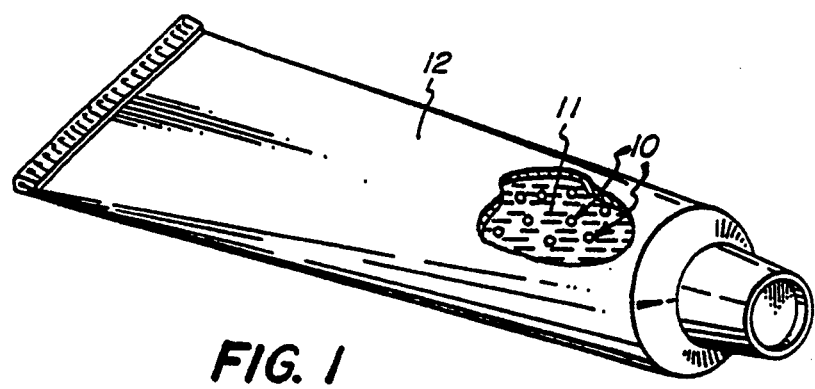
FIG. 1 is a perspective view of a tube containing the paste formulation of this invention.
Figure 2:
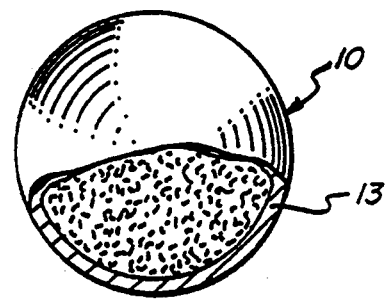
FIG. 2 is a microencapsulated component of the present invention.

The improved tooth and gum formulation comprises from 15 to 35% by weight of sodium bicarbonate, from 10 to 30% by weight of hydrated silica, from 3 to 11% of calcium peroxide, which according to this invention is microencapsulated in micro pellets 10 as shown in FIG. 2, homogeneously distributed throughout the paste composition 11 as noted in FIG. 1. The formulation also includes 0.125 to 3% by weight of fluoride, e.g. sodium fluoride, a sodium monofluorophosphate or stannous fluoride, and from 0.5 to 3% by weight of urea which may also be microencapsulated. These ingredients are mixed into a paste carrier comprising approximately from 40% to 78% by weight. The carrier may include a detergent, humectant (sorbitol), a thickening agent or binder, preservative, whitener, surfactant, tartar remover and a suitable flavoring agent. The dentifrice is compounded by mixing the ingredients of the base paste or carrier with the appropriate portions of the fluoride ingredient followed by mixing therewith the sodium bicarbonate followed by mixing therewith the specified quantity of silica and flavoring agent, with the microencapsulated calcium peroxide being the last ingredient added thereto. Upon completion of the mix, the formulation is then placed in a light resistant and moisture-proof container or tube 12 as shown in FIG. 1.

Optionally, the fluoride selected from the group consisting of one or more of sodium fluoride, sodium monofluorophosphate, or stannous fluoride ingredient may also be encapsulated as micro pellets and dispersed in the carrier or paste 11. The coating 13 for microencapsulating the calcium peroxide may be formed of an ethyl cellulose or other suitable coating which is capable of containing the calcium peroxide segregated until brushing is accomplished in the oral cavity. The fluoride component may be similarly microencapsulated. If more than one ingredient is microencapsulated, they can be optimally microencapsulated with coatings of different colors for identification purposes. The micro pellets may also be multi-colored in various hues.

In the formulation described, the micro pellets of calcium peroxide tend to adhere to the tissues and can remain in place for a relatively long period of time, effectively absorbing water from the saliva. The absorption of water from the saliva causes the ethylcellulose coating of the microencapsulation to swell, allowing the water in the saliva and the enzymes within the oral cavity to permeate the coating to react with the peroxide to release nascent oxygen to aid in debriding tissue and causing a bacteriocidal effect on anaerobic bacteria. The formulation also effects a foaming action which with brushing mechanically tends to raise any plaque and bacteria from incipient periodontal lesions to prevent them from releasing their distinctive destructive enzymes in and around the gingival pockets.

As the urea reaches the oral cavity, it disassociates into ammonia ($NH_3$) with the aid of the enzyme urease. The calcium peroxide in the paste, upon the release, disassociates in the environment within the oral cavity to produce hydrogen peroxide ($H_2O_2$), which in the presence of peroxidase and catalase, causes the release of free oxygen. The free oxygen and free ammonia produce a cidal effect on the bacteria to provide for an anti-caries and anti-plaque effect. The urea turns to $NH_3$ and carbonic acid by the enzyme urease. This raises the acidified plaque to a more neutral pH and reduces the rate of tooth demineralization to render the tooth more resistant to caries by fermented carbohydrates. In the formulation, the urea has an anti-caries and anti-plaque effect.

The silica portion of the formulation functions as a mild abrasive and polishing agent. It has also been found that hydrated silica renders sodium fluoride stable. It will be understood that other fluorides, e.g. stannous fluoride or sodium monofluorophosphates may be used in lieu of sodium fluoride.

The sodium bicarbonate ($NaHCO_3$) ingredient in the formulation also has a mild abrasive action on the tooth surface, when brushing, to effect the mechanical removal of dental plaque, bacteria, food particles and stains from the teeth surfaces. It also functions to neutralize mouth odors by absorption and tends to brighten the enamel of the tooth.

The fluoride ingredient combines chemically into the enamel structure of the teeth to form a fluor-apatite so as to cause the enamel to become harder to resist caries. This is achieved by rendering the enamel less likely to be demineralized by the acids formed by the adhering bacteria and their activity with sugar substances. Fluorides are also known to retard the rapidity of pre-existing dental caries.

The general formulation of tooth and gum paste comprises:

15 to 35% by weight of sodium bicarbonate which may include
a #325 grit
10 to 30% by weight of hydrated silica
3 to 11% by weight of microencapsulated calcium peroxide
0.5 to 3.0% by weight of urea
0.125 to 3% by weight of a fluoride
40 to 78% by weight of a carrier.

The carrier comprises a mixture of a detergent, a humectant (sorbitol) and a thickening agent or binder, whitener, surfactant, tartar remover, a sweetener, preservative, and a flavoring agent. Included in the carrier is glycerine to enhance a pleasant mouth feel. A preferred carrier may include 1 to 4% by weight of sorbitol, 1% to 3.85% by weight of sodium lauryle sulfate. The remainder of the carrier by weight may comprise miscellaneous binders which may include sweeteners, whitener and a preservative.

The thickening agent functions to prevent any separation of the liquid and the solid ingredients. The thickening agent or binder may comprise Carbopol 940P, gum tragacanth and gum karaya (natural), seaweed colloid—sodium alginate and synthetic cellulose, i.e. Na carboxymethylcellulose or methycellulose. A foaming agent such as sodium lauryle sulfate and sodium -N-layrylscrosenate is also included. The sweetener may be comprised of sodium saccharin, asparatame and/or a suitable flavoring ingredient such as mint, spearmint or the like.

The tooth and gum dentifrice thus functions as a tooth paste having anti-plaque, anti-tartar, oxygenation, stain-removing, antiseptic, odor inhibiting and tooth brightening characteristics.

The formulation consists of a dry mix which includes the sodium bicarbonate, the hydrated silica and the microencapsulated calcium peroxide.

The wet mix portion includes the glycerine, Urea, the fluoride, sorbitol, flavor, sweetener, tartar remover, and binder ingredients.

It is preferred that the solids be fine milled so as to pass through a #50 sieve. All equipment should be made of stainless steel or other non reactive material, and any type of moisture conditions which the manufacturing process may contribute are to be avoided.

A specific formulation of the tooth and gum paste comprises the following:

| | |
|---|---|
| 30-55% by weight | glycerine |
| 1-4% by weight | Sorbitol powder |
| 0.2-1% by weight | Carbopol 940 P |
| .10-.70% by weight | sodium benzoate |
| .125-3% by weight | sodium fluoride |
| .5-3% by weight | urea |
| 15-35% by weight | sodium bicarbonate |
| 10-30% by weight | hydrated silica |
| .5-2% by weight | titanium dioxide 3328 |
| 3.5-11% by weight | $CaO_2$ microencapsulated |
| .5-2% by weight | flavoring agent |
| .1-3.85% by weight | surfactant |

In another form of the invention, 1 to 10% by weight of microencapsulated hydrogen peroxide ($H_2O_2$) may be substituted in the above formulation for the microencapsulated calcium peroxide.

It will be understood that stannous fluoride or sodium monofluorophosphates may be substituted for the sodium fluoride in the above formulation.

A specific formulation embodying the invention includes:

| |
|---|
| 15% by weight of Sodium Fluoride |
| 1.5% by weight of urea |
| 15.% by weight of |
| Sodium bicarbonate or potassium bicarbonate |
| 5.% by weight of calcium peroxide (microencapsulated) |
| 78.35% by weight of a carrier |
| 100% |

Another specific formulation includes:

| |
|---|
| .20% by weight of sodium fluoride |
| 2.% by weight of urea |
| 25.% by weight of |
| Sodium bicarbonate or potassium bicarbonate |
| 8.5% by weight of calcium peroxide (microencapsulated) |
| 64.3% by weight of carrier |
| 100% |

Another specific formulation may include:

| |
|---|
| .25% by weight of sodium fluoride |
| 3.% by weight of urea |
| 35.% by weight of sodium or potassium bicarbonate |
| 11.% by weight of calcium peroxide (microencapsulated) |
| 50.75% by weight of paste carrier |
| 100% |

The carrier or paste composition of the foregoing specific formulations include glycerine, humectant, thickener, preservative, whitener, flavoring agent, a surfactant, and hydrated silica.

The combination of the foregoing noted ingredients form an effective and stable paste composition that contains sodium bicarbonate, urea, a stable peroxide and a fluoride mixed in a single component paste, that becomes active in use when the paste comes in contact with the saliva in the oral cavity to result in a chemical and mechanical action for removing plaque, tooth stain, tartar and inhibiting bacterial flora that contribute to the incidence of periodontal disease, dental caries and undesirable mouth odors.

A preferred method for compounding the tooth and gum paste described herein is to combine the glycerine, sorbitol powder and Carbopol 940P to form a first phase or mix which is heated to 60° C. The ingredients of the second phase, i.e. Sodium benzoate, sweetener, e.g. sodium saccharine, sodium fluoride and urea are then added to the heated first phase by mixing.

The third phase comprising the baking soda, preferably Grade 1, hydrated silica and whitener are mixed and then added as a mix to the heated, previously mixed first and second phases and vacuum mix for approximately 30 minutes. The combined first three phases are then cooled to approximately 30° to 40° C. To the cooled mixture of phases 1, 2 and 3, the balance of the ingredients are added thereto with a slow mixing action, the microencapsulated peroxide ingredient being the last added ingredient by slow mixing by blade.

If desired, the compositions described herein may be further fortified by the addition of either natural or synthetic enzymes consisting of catalase, urease and peroxidase.

The preferred hydrated silica may be a Zeodent 113 or Zeodent 165 or a combination thereof. The surfactant referred to may comprise Stepanol WA-100 or a sodium lauryle sulfate.

The microencapsulated peroxide may consist of a blend of 75% by weight of calcium peroxide and 25% by weight of calcium hydroxide. The peroxide constituent is provided with an ethylcellulose coating that consists of 6.5% by weight of the finished product. The optimum coating levels appear to be between 5 and 7.5% by weight. The preferred microcapsules range between 10 to 200 microns.

The microencapsulation of the calcium peroxide and/or the peroxide blend as described is effected by mixing the ethylcellulose with cyclohexane in a mixing vessel at a temperature of 50° C. The temperature of the mix is then raised to 70° C. over a period of 20 to 30 minutes. The peroxide to be used is then weighed and added to the mix and the temperature raised to 80° C. over a period of time and held at 80° C. for one hour. The system is then allowed to cool rapidly to 20°-40° C. Thereafter, the capsules are then removed, washed, filtered and air dried.

There are a number of materials that can be added to the ethylcellulose microencapsulating material to aid in the encapsulating process. Examples of such materials are polysobutylene, dimethyl silicone, synthetic wax (ethylene polymer), polyethylene and butyl rubber. The percentages of these materials can range from 1% to 99% in combination with ethylcellulose and each other. The ratio of the encapsulation material to solvent can range from 1% to 99% in a similar mix with the processing aid.

While the present invention has been described with respect to several embodiments, it will be understood that variations and modifications can be made without departing from the spirit or scope of the invention. For example, calcium bicarbonate may be substituted for the sodium bicarbonate in the formulations described. Also, the percentages of the various ingredients may vary within the defined ranges noted.

What is claimed is:

1. A tooth and gum dentifrice composition in the form of a single component stable paste for controlling and minimizing incipient periodontal disease and for aiding the reduction of plaque and undesirable mouth odors comprising approximately 15 to 35% by weight of sodium bicarbonate, approximately 10 to 30% by weight of hydrated silica, approximately 3.5 to 11% by weight of calcium peroxide in microencapsulated form, said microencapsulated calcium peroxide including a blend of calcium peroxide and calcium hydroxide, approximately 0.5 to 3% by weight of urea, approximately 0.125 to 3.0% by weight of sodium fluoride and approximately 40 to 78% by weight of a carrier that is free of water, said sodium bicarbonate, hydrated silica, microencapsulated calcium peroxide, urea and sodium fluoride being mixed in said carrier whereby upon contact with the saliva in the oral cavity, said urea disassociates into ammonia and the calcium peroxide in the presence of the aqueous environment of the oral cavity combine to produce hydrogen peroxide, which in the presence of peroxidase and catalase causes the release of free oxygen thereby enhancing a cidal effect on bacteria to produce an anti-caries and anti-plaque effect.

2. A tooth and gum dentifrice composition in the form of a single stable paste component for controlling and minimizing incipient periodontal disease and for aiding the reduction of plaque, tartar and undesirable mouth odors comprising

| | |
|---|---|
| 30 to 55% | by weight of glycerine |
| 1 to 4% | by weight of sorbitol powder |
| 2 to 1% | by weight of Carbonol .940 P |
| .10 to .70% | by weight of sodium benzoate |
| .125 to 3% | by weight of sodium fluoride |
| .5 to 3% | by weight of urea |
| 15 to 35% | by weight of sodium bicarbonate |
| 10 to 30% | by weiaht of hydrated silica |
| .5 to 2% | by weight of titaniumldioxide 3328 |
| 3.5 to 11% | .by weight of calcium peroxide |
| .5 to 2% | by weight of flavoring agent |
| .1 to 2% | by weight of surfactant tartar remover | whereby said calcium peroxide is microencapsulated of a size ranging between 10 to 200 microns, wherein the microencapsulated calcium peroxide comprises a blend of 75% by weight of calcium peroxide and 25% by weight of calcium hydroxide.

3. A method of formulating a tooth and gum dentrifice in the form of a single stable paste component containing a peroxide and a bicarbonate ingredient comprising the steps of:

combining glycerine, sorbitol powder and Carbopol 940P by mixing to form a first phase mix;

heating said first phase mix to approximately 60° C.;

combining sodium benzoate, a sweetener, sodium fluoride and urea by mixing to form a second phase mix;

adding said second phase mix to said first phase heated mix and mixing the two phases together;

combining sodium bicarbonate, hydrated silica and a whitener to form a third phase mixture;

adding said third phase mixture to the heated combined first and second phase mixes;

vacuum mix the combined first, second and third phases for approximately thirty (30) minutes;

cool the vacuum mixed first, second and third phase mixes to temperature ranging between 30 to 40° C.;

add the flavoring agent, surfactant and the microencapsulated calcium peroxide to the vacuum mixed said first, second and third phase mixes by a slow mixing action whereby the microencapsulated calcium peroxide is the last added ingredient.

4. A tooth and gum dentrifice composition in the form of a stable single component paste formulation comprising:

| | |
|---|---|
| .15 to .25% | by weight of sodium fluoride |
| 1.5 to 3% | by weight of urea |
| 15 to 35% | by weight of a bicarbonate selected from a group consisting of one or more of calcium bicarbonate, sodium bicarbonate and potassium bicarbonate |
| 5 to 11% | by weight of calcium peroxide whereby said calcium peroxide is microencapsulated with a water permeable coating, and |
| 50.75 to 78.35% | by weight of a carrier, | and wherein said microencapsulated calcium peroxide comprises a blend of calcium peroxide and calcium hydroxide.

5. A tooth and gum dentrifice as defined in claim 4 wherein said microencapsulated calcium peroxide comprises a blend of 75% by weight of calcium peroxide and 25% by weight of calcium hydroxide.

6. A tooth and gum dentrifice as defined in claim 4 wherein said carrier includes 10 to 30% by weight of hydrated silica.

* * * * *